United States Patent [19]
Allen

[11] Patent Number: 5,624,422
[45] Date of Patent: Apr. 29, 1997

[54] ABSORBENT ARTICLE HAVING AN EXTENDIBLE SPLIT CORE

[75] Inventor: Patrick J. Allen, Cincinnati, Ohio

[73] Assignee: The Procter & Gamble Company, Cincinnati, Ohio

[21] Appl. No.: 310,604

[22] Filed: Sep. 22, 1994

[51] Int. Cl.$^6$ .................................................. A61F 13/15
[52] U.S. Cl. ................................. 604/385.1; 604/378
[58] Field of Search ......................... 609/385.1, 385.2, 609/358, 394, 396; 604/378, 381, 382, 384, 386

[56] References Cited

U.S. PATENT DOCUMENTS

| | | |
|---|---|---|
| 19,418 | 2/1858 | Hall . |
| 2,004,088 | 1/1935 | Alsop . |
| 2,532,029 | 3/1947 | Medoff . |
| 2,690,749 | 8/1954 | Nelson . |
| 3,532,093 | 10/1970 | Lovret . |
| 3,665,920 | 5/1972 | Davis . |
| 4,285,342 | 8/1981 | Mesek . |
| 4,475,912 | 10/1984 | Coates .................. 604/385 |
| 4,642,109 | 2/1987 | Bradley et al. .......... 604/385 |
| 4,655,760 | 4/1987 | Morman et al. ......... 604/385 |
| 4,662,877 | 5/1987 | Williams ................. 604/385 |
| 4,681,577 | 7/1987 | Stern ...................... 604/378 |
| 4,681,579 | 7/1987 | Toussant et al. ........ 604/385 |
| 4,695,278 | 9/1987 | Lawson .................. 604/385 |
| 4,699,620 | 10/1987 | Bernardin ............... 604/385 |
| 4,701,170 | 10/1987 | Wilson et al. ........... 604/385 |
| 4,701,171 | 10/1987 | Boland et al. ........... 604/385 |
| 4,701,173 | 10/1987 | Zehner et al. ........... 604/385 |
| 4,701,175 | 10/1987 | Boland et al. ........... 604/385 |
| 4,704,114 | 11/1987 | Wilson et al. ........... 604/385 |
| 4,704,116 | 11/1987 | Enloe ..................... 604/385 |
| 4,710,187 | 12/1987 | Boland et al. ........... 604/385 |
| 4,718,900 | 1/1988 | Boland et al. ........... 604/385 |
| 4,718,901 | 1/1988 | Singheimer ............. 604/385 |
| 4,731,066 | 3/1988 | Korpman ................ 604/366 |
| 4,747,846 | 5/1988 | Boland et al. .......... 604/38 A |
| 4,781,711 | 11/1988 | Houghton et al. ...... 604/378 |
| 4,816,025 | 3/1989 | Foreman ................ 604/385.2 |
| 4,850,990 | 7/1989 | Huntoon et al. ....... 604/385.2 |
| 4,892,536 | 1/1990 | DesMarais et al. ..... 604/385.2 |
| 4,892,598 | 1/1990 | Stevens et al. ........... 156/91 |
| 4,895,568 | 1/1990 | Enloe .................... 604/385.2 |
| 4,908,804 | 3/1990 | Douglas, Sr. .......... 604/385.2 |
| 4,909,803 | 3/1990 | Aziz et al. ............. 604/385.2 |
| 4,935,021 | 6/1990 | Huffman et al. ....... 604/385.1 |
| 4,957,795 | 9/1990 | Riedel ..................... 428/74 |
| 4,968,312 | 11/1990 | Khan ...................... 604/388 |
| 4,990,147 | 2/1991 | Freeland ................ 604/385.2 |
| 5,032,120 | 7/1991 | Freeland et al. ...... 604/385.2 |
| 5,037,416 | 8/1991 | Allen et al. ............ 604/385.1 |
| 5,062,840 | 11/1991 | Holt et al. .............. 604/385.1 |
| 5,102,711 | 4/1992 | Keller et al. ............. 428/71 |
| 5,151,092 | 9/1992 | Buell et al. ............ 604/385.2 |
| 5,171,263 | 12/1992 | Dreier et al. ........... 604/369 |
| 5,207,660 | 5/1993 | McQueen .............. 604/385.1 |
| 5,269,775 | 12/1993 | Freeland et al. ...... 604/385.2 |
| 5,330,459 | 7/1994 | Lavon et al. .......... 604/385.1 |
| 5,462,541 | 10/1995 | Bruemmer ............ 604/385.1 |

FOREIGN PATENT DOCUMENTS

| | | |
|---|---|---|
| 0486006 | 5/1992 | European Pat. Off. . |
| 2495899 | 6/1982 | France ................... 604/385.1 |
| 2561078 | 9/1985 | France ................... 604/385.1 |
| 0433951A2 | 12/1990 | Germany . |

*Primary Examiner*—Mark O. Polutta
*Attorney, Agent, or Firm*—Mary Pat McMahon; Larry L. Huston; Jacobus C. Rasser

[57] ABSTRACT

A disposable article having a void area for isolation of fecal material is disclosed. The void is created by having a split absorbent core and at least one elastically extendible topsheet/backsheet panel proximate to the split. The void is created and adjusted by the amount of extension of the topsheet/backsheet proximate to the split.

8 Claims, 5 Drawing Sheets

ABSORBENT ARTICLE HAVING AN EXTENDIBLE SPLIT CORE

FIELD OF THE INVENTION

The present invention relates to disposable absorbent articles, and more particularly to disposable absorbent articles which isolate and minimize the migration of fecal material deposited thereon.

BACKGROUND OF THE INVENTION

Disposable absorbent articles, such as diapers, are well known in the art. Disposable absorbent articles retain and absorb body exudates, such as urine and fecal material deposited thereon.

Significant advances have been made in the art relative to absorbing and retaining urine deposits. For example, disposable absorbent articles seldom leak and may be relatively thin due to the incorporation of absorbent gelling materials.

However, fewer attempts have been made in the art to handle deposits of fecal material in disposable absorbent articles. Fecal material has the undesirable problems of smearing onto the wearer's skin, causing epidermal irritation and complicating the task of cleaning the wearer when the soiled diaper or other disposable absorbent article is removed.

To overcome these problems, certain attempts have been made in the art to isolate the fecal material from the skin of the wearer. Such attempts include providing cups which attempt to circumscribe the anal opening, the genitalia, or both in an attempt to isolate these, regions of the wearer's body. These attempts can be uncomfortable for the wearer and require precise positioning of the cup.

In still another attempt, resilient barriers extending transversely or longitudinally have been placed below the topsheet of the diaper. But this arrangement suffers from the drawback that fecal material deposited on the topsheet above the barrier, can migrate and still cause the aforementioned problems. This arrangement simply does not provide the abrupt discontinuity necessary to obstruct migration of fecal material deposited on the topsheet of the diaper.

Furthermore, such an arrangement may even be ineffective in preventing excessive transverse migration of the fecal material. A barrier disposed below the topsheet cannot be easily joined to longitudinally extending barrier leg cuffs, which, as are well known in the art, minimize leakage from the diaper. Thus, fecal material which is channeled towards transverse migration by the barrier may be transported to the perimeter of the diaper and breach the perimeter, causing leakage.

Other attempts have been made in the art to provide a void or hole into which the fecal material is deposited and retained (hopefully), so that the location of the fecal material is limited to the position of the void or hole. Examples of such attempts are found in U.S. Pat. No. 4,662,877 issued May 5, 1987, to Williams; U.S. Pat. No. 4,892,536 issued Jan. 9, 1990, to DesMarais et al.; U.S. Pat. No. 4,968,312 issued Nov. 6, 1990, to Khan; U.S. Pat. No. 4,990,147 issued Feb. 5, 1991, to Freeland; U.S. Pat. No. 5,062,840 issued Nov. 5, 1991, to Holt et al.

Accordingly, it is an object of this invention to provide a disposable absorbent article having an extendible absorbent split core to isolate and minimize the migration of fecal material, thereby reducing epidermal contact with the fecal material and minimizing cleaning by the caretaker. It is also an object of this invention to provide an absorbent article having both an elasticized panel topsheet and expandable or elasticized panel back sheet to provide a greater void volume to isolate fecal material from the wearer.

BRIEF DESCRIPTION OF THE DRAWINGS

While the specification concludes with claims particularly pointing out and distinctly claiming the present invention, it is believed the same will be better understood from the following description taken in conjunction with the associated drawings in which like reference numerals represent the same component:

FIG. 2 are fragmentary sectional views taken along section lines A, B and C; of FIG. 1.

BRIEF SUMMARY OF THE INVENTION

The present invention comprises a disposable absorbent article, such as a diaper. The disposable absorbent article has a partially liquid pervious topsheet with an outwardly oriented body facing surface which is oriented towards the wearer while in use, a core facing surfaced opposed to the body facing surface, at least one passageway and at least one elastically extendible panel. The disposable absorbent article further comprises a liquid impervious backsheet with at least one elastically extendible back panel and that is at least partially peripherally joined to the topsheet. Lastly, the absorbent article comprises a split absorbent core intermediate to the topsheet and the backsheet.

The disposable absorbent article further comprises a void positioned between the body facing surface of the topsheet and backsheet. The void is created by dividing the absorbent core. As the topsheet and bottom sheet are adjusted to fit the wearer the absorbent core is divided to create a void. Fecal material passes through the passageway of the topsheet and is deposited into and isolated within the void created between the topsheet and backsheet of the disposable absorbent article.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants or incontinent persons about the lower torso of the wearer. It should be understood, however, that the present invention is also applicable to other absorbent articles such as incontince briefs, incontince undergarments, diaper holders and liners, certain feminine hygiene garments, and the like.

Figure 1:
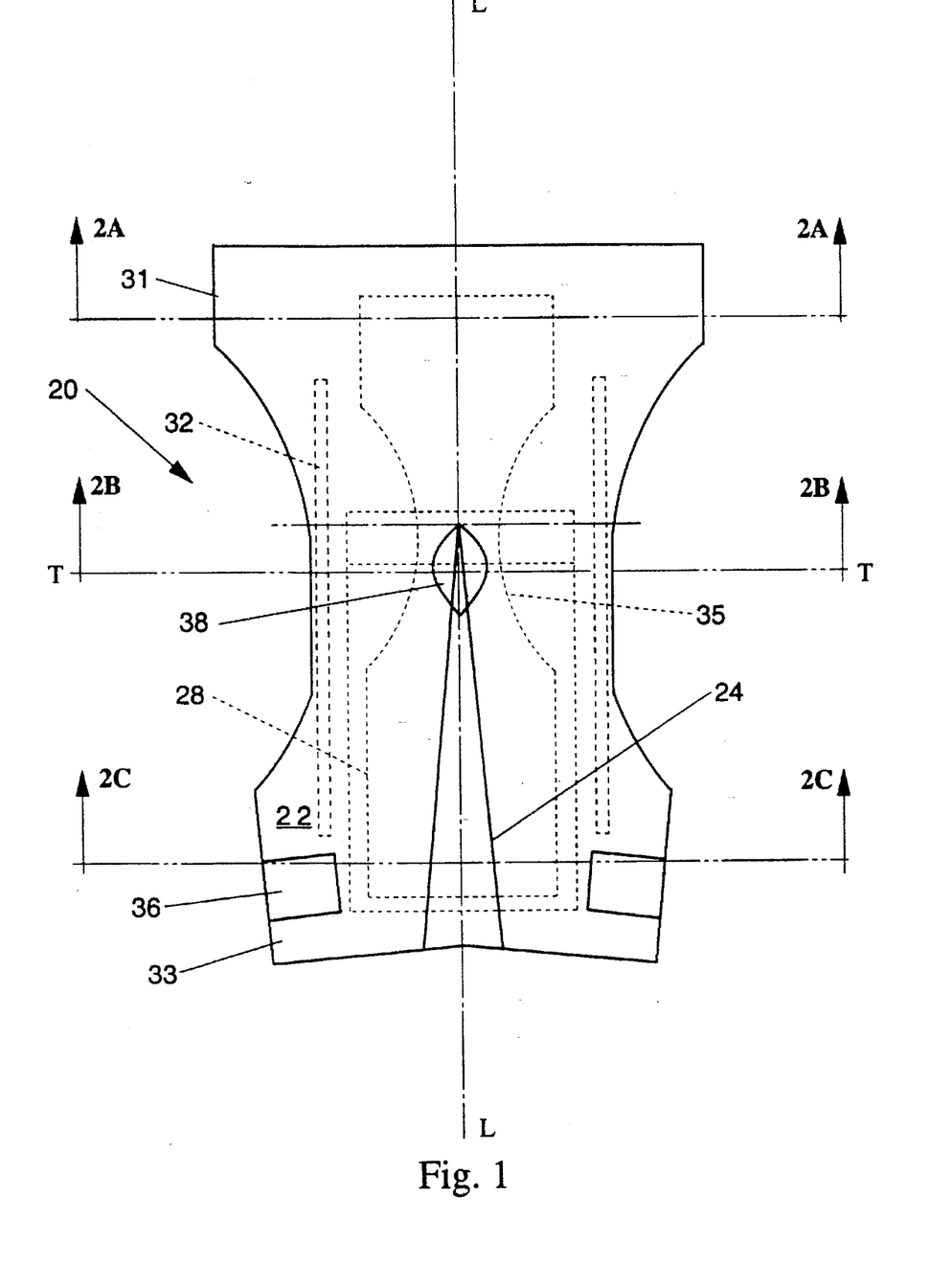
FIG. 1 is a top plan view of a disposable absorbent article according to the present invention, partially cutaway, and having the foam cap omitted for clarity and having no elastic induced contraction.

FIG. 1 is a plan view of the diaper 20 of the present invention in its flat-out, uncontracted state (i.e., with elastic induced contraction pulled out) with the portion of the diaper 20 which faces or contacts the wearer, the inner surface, oriented towards the viewer. As shown in FIG. 1, the diaper 20 preferably comprises a liquid pervious topsheet 22; a partially liquid impervious backsheet 26 joined with the topsheet 22; and absorbent core 28 positioned between the topsheet 22 and the backsheet 26; a fastening system generally multiple designated as 36.

The topsheet 22 of the diaper 20 has an outwardly oriented body facing surface which faces (and usually contacts) the wearer while the diaper 20 is in use and a core facing surface opposed to the body facing surface. The body facing surface of the topsheet 22 of the diaper 20 comprises that portion of the diaper 20 which is positioned adjacent the wearer's body during use (i.e., the inner surface generally is formed by both at least a portion of the topsheet 22 and other components joined to the topsheet 22). The diaper 20 further has a first waist region 31 oriented towards the front of the wearer while the diaper is in use, a second waist region 33 longitudinally opposite the first waist region 31, a crotch region 35 positioned between the first waist region 31 and the second waist region 33, and a periphery which is defined by the outer edges of the diaper 20.

The diaper 20 has a longitudinal axis L—L which divides the diaper 20 into left and right halves, and which divides the standing wearer into left and right body halves. The diaper 20 further comprises a transverse axis T—T orthogonal to the longitudinal axis L—L which divides the diaper 20 into a front portion and a rear portion. Orthogonal to the mutually perpendicular longitudinal axis L—L and transverse axis T—T, is a Z-direction axis, which extends outwardly from the plane of the diaper 20.

A component of the diaper 20 is considered to be transversely oriented, and hence "transverse" if such component forms an angle of ±45 degrees or less with the transverse centerline T—T. Similarly, a component is considered to be longitudinally oriented, and hence "longitudinal" if such component forms an angle of ±45 degrees or less with the longitudinal axis L—L.

FIG. 1 shows a preferred embodiment of the diaper 20 in which the topsheet 22 and the backsheet 26 have length and width dimensions generally larger than those of the absorbent core 28. The topsheet 22 and the backsheet 26 extend beyond the edges of the absorbent core 28 to thereby form the periphery of the diaper 20. While the topsheet 22, the backsheet 26, and the absorbent core 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and application Ser. No. 07/715,152, allowed, "Absorbent Article With Dynamic Elastic Waist Feature Having a Predisposed Resilient Felxural Hinge", Kenneth B. Buell et al. filed Jun. 13, 1991; All of which are incorporated herein by reference.

Although not shown in FIG. 1, the absorbent core is split, preferably in the rear section, to be intermediate to the topsheet panel 24 to create a void area in the disposable absorbent article.

The topsheet 22 is positioned adjacent the body surface of the absorbent core 28 and is preferably at least partially peripherally joined thereto to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 22 and the backsheet 26 are joined directly to each other in the diaper periphery and are indirectly joined together as a result of their joinder to the absorbent core 28 by suitable attachment means (not shown).

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or posts of adhesive. Adhesives which have been found to be satisfactory are manufactured by H.B. Fuller Company of St. Paul, Minn. and are marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173, issued to Sprague, Jr. on Oct. 7, 1975; U.S. Pat. No. 4,785,996 issued to Ziecker et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g. urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or non woven material, polymeric films such as thermoplastic films of polyethylene or polypropylene, or composite materials such as a film-coated non woven material. Preferably, the backsheet is a thermoplastic film having a thickness of from about 0.012 mm (0.5 rail) to about 0.051 mm (2.0 mils). Particularly preferred materials for the backsheet 26 include X#8220 blown films and X#5474 cast films as manufactured by Tredegar Industries, Inc. of Terre Haute, Ind. The backsheet 26 is preferably embossed and/or matte finished to provide a more cloth like appearance. Further, the back sheet 26 may permit vapors to escaped from the absorbent core 28 (i.e. breathable) while still preventing exudates from passing through the backsheet 26. Lastly, the backsheet 26 may be made entirely of elastically extensible material, preferably the backsheet 26 has at least one an extensible panel material proximate to the topsheet elastically extensible panel 24.

The topsheet 22 is compliant, soft feeling, and non-irritating to the wearer's skin. Further, the topsheet 22 is liquid pervious permitting liquids (e.g. urine) to readily penetrate through its thickness. A suitable topsheet may be manufactured from a wide range of materials, such as porous foams; reticulated foams; apertured plastic films; or woven or non woven webs of natural fibers (e.g., wood or cotton fibers), synthetic fibers (e.g., polyester or polypropylene fibers), or a combination of natural and synthetic fibers. Preferably, the topsheet 22 is made of a hydrophobic material to isolate the wearer's skin from liquids contained in the absorbent core 28. There are a number of manufacturing techniques which may be used to manufacture the topsheet 22. For example, the topsheet 22 may be a non woven web of fibers spun bonded, carded, wet-laid, melt blown, hydroentangle, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company of Walpole, Mass. under the designation P-8.

In accordance with one aspect of the present invention, the topsheet 22 is elastically extensible in at least one direction. As used herein, the term "elastically extensible" means able to be stretched from the free length at least about 50 percent for a period of about 15 seconds and to return to within about 10 percent of the free length within about 5 minutes of the release of the force which causes such elongation to occur. Generally the principal axis of elongation, in which the laminate of the topsheet 24 is elastically extensible is generally parallel to the longitudinal axis L—L, although all or a portion of the topsheet 24 may be elastically extensible in more than one direction or in a direction generally orthogonal the longitudinal axis L—L.

Preferably, the topsheet 22 of the present invention is elastically extensible at least about 350 percent elongation without rupture and more preferably to at least about 450 percent elongation without rapture, although a topsheet 22 which as a lesser elongation without rupture, such as 50 to 100 percent is suitable. As used herein, the term "rupture" means tearing, fracturing, or breaking into two or more subparts. This property provides for conforming to the shape of the wearer's body and maintaining close contact to the skin of the wearer. Also a topsheet 22 which is relatively highly extensible can comfortably fit a larger range of size of wearer. Exemplary elastically extendible material is described further in U.S. Pat. No. 5,037,416, issued to Allen et al. on Aug. 6, 1991 which is incorporated herein by reference.

The topsheet 22 further comprises at least one passageway 38 wherein exudates such as fecal material may pass through to the absorbent core. This void 38 which may be elasticized permits the exudates to be isolated from the wearer's skin.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred as airfelt. Examples of other suitable absorbent materials include creped cellulose wadding; melt blown polymers including conform; chemically stiffened, modified or cross-linked cellulosic fibers; tissue including tissue wraps and tissue laminates; gelling materials; or any equivalent material or combinations of materials. The configuration and construction of the absorbent core may also be varied (e.g., the absorbent core may have varying caliper zones, a hydrophilic gradient, a super absorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the, size and absorbent capacity of the absorbent core 28 may be varied to accommodate wearers ranging from infants through adults. Exemplary absorbent structures for use as the absorbent core 28 are described in U.S. Pat. No. 4,610, 678 entitled "High-Density Absorbent Structures" issued to Weisman et al. On Sep. 9, 1986; U.S. Pat. No. 4,673,402 entitled "Absorbent Articles with Dual Layered Cores" issued to Weisman et al. on Jun. 16, 1987; U.S. Pat. No. 4,888,231 entitled "Absorbent Core Having a Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alermany et al. on May 30, 1989. Each of these patents are incorporated herein by reference.

The diaper preferably further comprises elasticized barrier leg cuffs 32 for providing improved containment of liquids and other body exudates. Each elasticized barrier leg cuff 32 may comprise several different embodiments for reducing the leakage of body exudates for the leg regions of the diaper 20. U.S. Pat. No. 4,909,803 entitled "Disposable Absorbent Article Having Elasticized Flaps" issued to Aziz et al. on Mar. 20, 1990, describes a disposable diaper 20 having "stand-up" elasticized flaps (barrier leg cuffs 32) to improve the containment of the leg regions of the diaper 20. U.S. Pat. No. 4,695,278 entitled "Absorbent Article Having Dual Cuffs" issued to Lawson on Sep. 22, 1987, describes a disposable diaper 20 having dual cuffs including both a gasketing cuff and a barrier cuff 32. Both of these patents are incorporated herein by reference for the purpose of showing suitable exemplary constructions for the barrier leg cuffs 32.

Figure 2A:
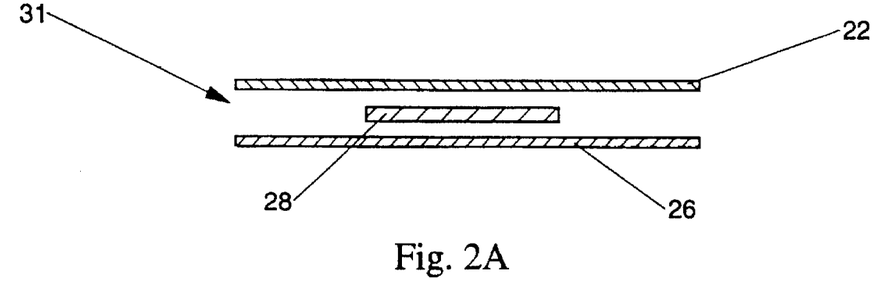
Figure 2B:
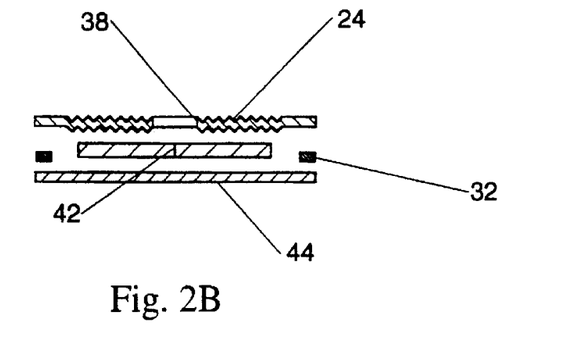
Figure 2C:
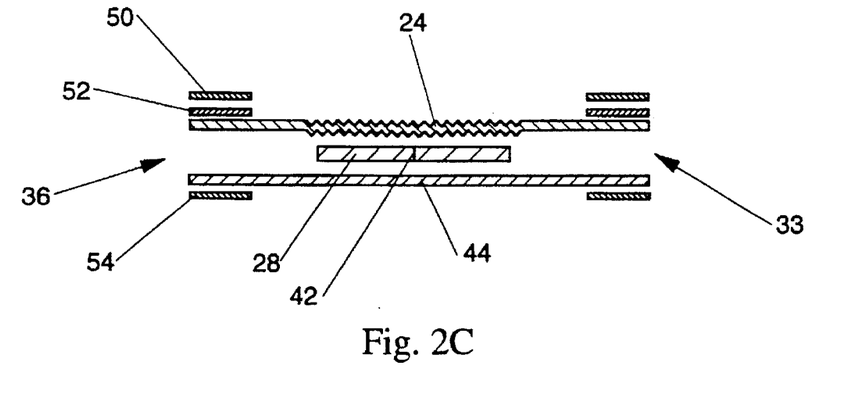

Referring to FIG. 2 (A, B and C are sectional views of FIG. 1 with portions of the structure being cut away to more clearly show the construction of the diaper), the A section comprises a topsheet 22, an absorbent core 28 and a backsheet 26. Section B comprises an opening 38 in the topsheet 22, an elasticized panel section 24 of the topsheet 22, a split 42 in the absorbent core 28 and an elasticized panel section 44 of the backsheet 26. The opening 38 is preferably elasticized to ensure better fit and as a barrier. Lastly, section C comprises an elasticized panel 24 of the topsheet 22, a split 42 of the absorbent core 28 and an elasticized panel 44 of the backsheet 26. In a preferred embodiment, as shown in FIGS. 1, 2B, and 2C, elasticized panel 24 of topsheet 22 increases in transverse dimension as the second, preferably the rear, waist region 33 is approached.

The diaper 20 is preferably applied to a wearer by positioning one of the waist regions 31 or 33, preferably the second waist region 33 (which typically has the fastening system 36), under the wearer's back and drawing the remainder of the diaper 20 between the wearer's legs so that the other waist region 31, preferably the first waist region 31, is positioned across the front of the wearer. The fastener tape 50 are positioned across the front of the wearer. The fastener tape tabs 50 of the fastening system 36 are then released from the release portion 52. The diaperer then wraps the elasticized side panel around the wearer, while still grasping the tab portion. The elasticized side panels will typically be extended and tensioned during this aeration so as to conform to the size and shape of the wearer. The fastening tab 50 is secured to the outer surface of the diaper to effect a side closure.

Figure 3:
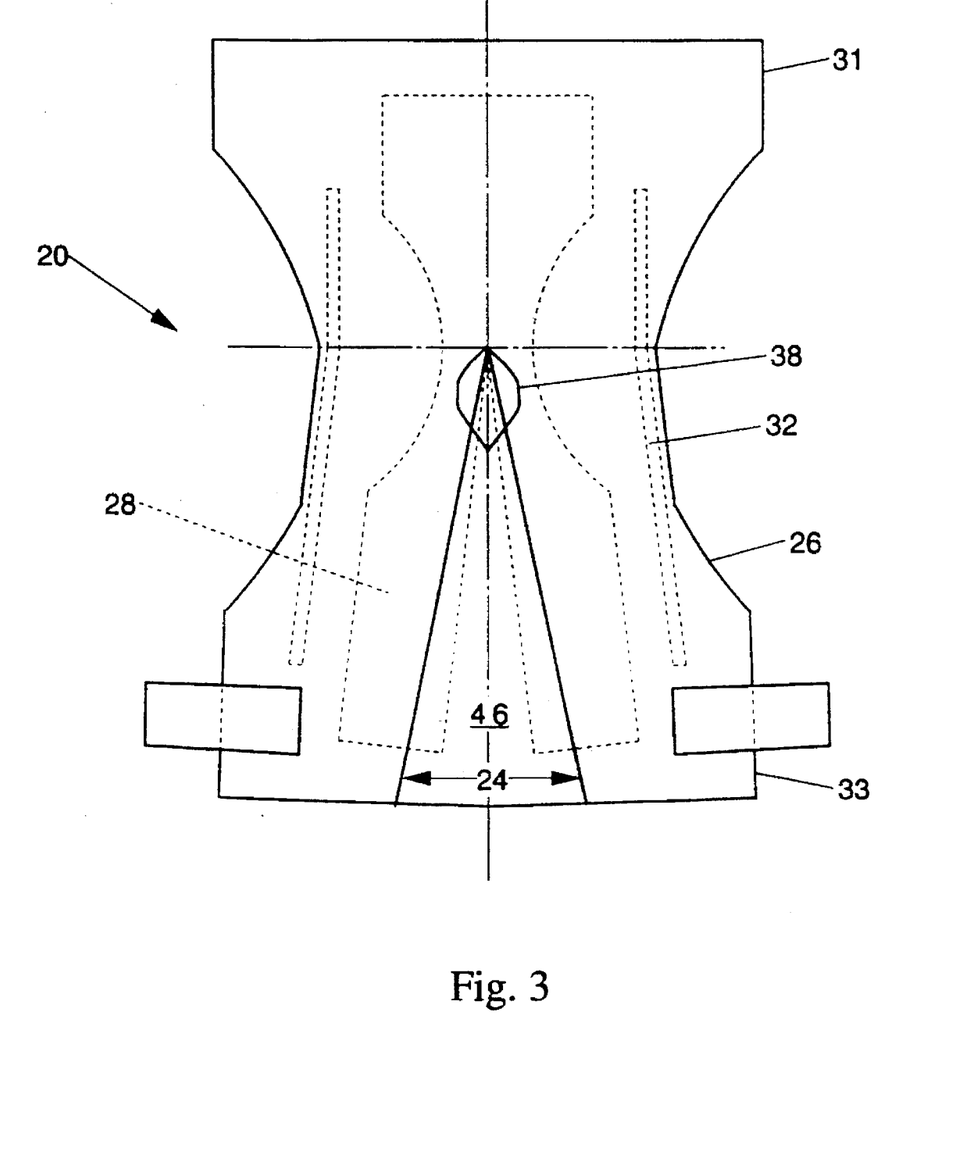
FIG. 3 is a top plan view of a disposable absorbent article according to the present invention, whose rear section has been expanded as it would be in wear on a wearer to show the separation of the split or segmented absorbent core and the resulting void that is created.

As illustrated in FIG. 3, a void 46 is created between the elasticized topsheet panel 24 and the backsheet panel when pressure is applied to the fastening tabs 50. This void, 46, which, as shown, diverges as it approaches the second, preferably the rear, waist region 33, is adjustable to the size or the wearer and/or the positioning of the tabs on the topsheet 22. The absorbent core 28 preferably is attached to non elasticized areas of the topsheet 22 and the bottomsheet 26.

Figure 4:
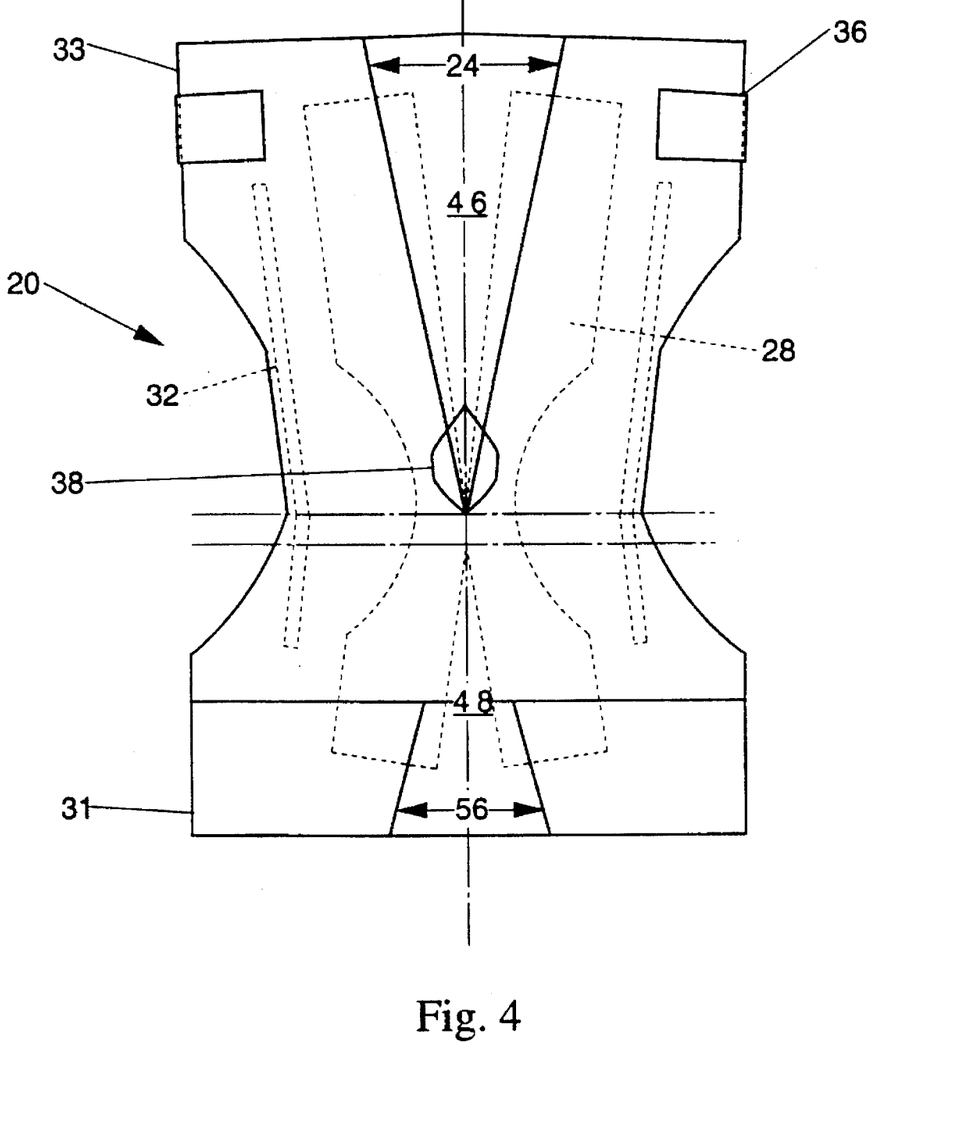
FIG. 4 is an alternate top plan view of a disposable absorbent article according to the present invention, whose front and rear panels have been expanded to show a rear and front absorbent core void.

FIG. 4 is an alternate embodiment of the present invention further comprising a void 48 in the front of the diaper 20. This void is created similar to the creation of the rear void 46 wherein there is a second elasticized panel 56 in the topsheet 22. Pressure is exerted on either side of the waist region 31 of the diaper 20 to create the front void 48. This front void 48 is particularly preferred for isolation of urine and/or fecal material, most preferably urine. This additional area for urine isolation allows for maximum acquisition of urine in the diaper 20 and away from the wearer.

Figure 5:
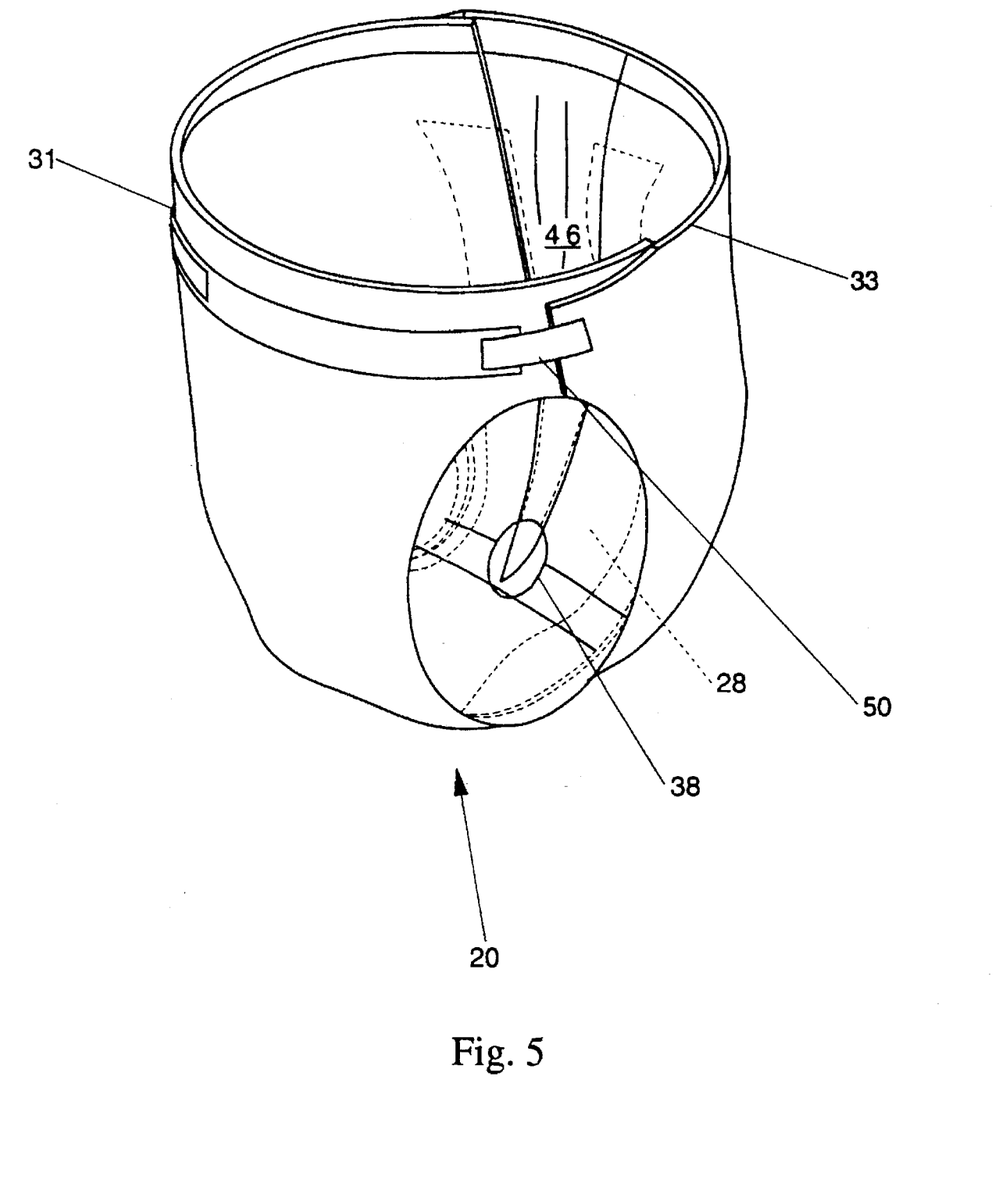
FIG. 5 is a perspective view of a disposable absorbent article according to the present invention as would be positioned on a wearer.

An example of a disposable article as would be positioned on a wearer is seen in FIG. 5. The diaper 20 is preferably applied to a wearer by positioning one of the waist regions 31 or 33, preferably the second waist region 33 (which typically has the fastening system 36), under the wearer's back and drawing the remainder of the diaper 20 between the wearer's legs so that the other waist region 31, is positioned across the front of the wearer. The fastening tape tabs 50 of the fastening system are then released from the release portion. The diaperer then wraps the elasticized side panel around the wearer, while typically be extended and tensioned during this operation so as to conform to the size and shape of the wearer and create the rear void 46. The fastening tab 50 is secured to the outer surface of the diaper 20 to effect a side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a longitudinal axis, a transverse axis orthogonal thereto and longitudinally opposed front and rear waist regions, said disposable absorbent article comprising:

a substantially liquid pervious topsheet having opening and at least one elastically extendible panel, said panel spanning said longitudinal axis and increasing in transverse dimension as said rear waist region is approached; a liquid impervious backsheet at least partially peripherally joined to said topsheet and having at least one extendible panel corresponding in position to said panel of said topsheet; and an absorbent core intermediate said topsheet and said backsheet, said core having at least one longitudinal split, said split extending through a transverse edge of said core and diverging as said rear waist region is approached and corresponding in position to said topsheet panel and said backsheet panel, whereby fecal material deposited through said opening may cause elastic extension of said panels, and is isolated from said topsheet.

2. A disposable article according to claim 1 wherein said split extends into a rear portion of said disposable absorbent article.

3. A disposable article according to claim 2 wherein said topsheet comprises one elastically extendible panel intermediate to said split.

4. A disposable article according to claim 3 wherein said absorbent core is attached approximate to said split to an extendible surface of topsheet or said backsheet.

5. A disposable article according to claim 2 wherein said backsheet comprises one elastically extendible panel intermediate to said split core.

6. A disposable article according to claim 2 wherein said topsheet and said backsheet comprise elastically extendible material.

7. A disposable article according to claim 2 further comprising a second split of said absorbent core extending into a front portion of said disposable absorbent article.

8. A disposable article according to claim 7 wherein said topsheet and said backsheet each have one elastically extendible rear panel intermediate to said rear split and one elastically extendible front panel intermediate to said front split.

* * * * *

UNITED STATES PATENT AND TRADEMARK OFFICE
CERTIFICATE OF CORRECTION

PATENT NO. : 5,624,422

DATED : April 29, 1997

INVENTOR(S) : PATRICK J. ALLEN

It is certified that error appears in the above-identified patent and that said Letters Patent is hereby corrected as shown below:

Column 1, line 31, "these," should read -- these --.

Column 4, line 65, "rail" should read -- mil --.
Column 5, line 48, "rapture," should read -- rupture, --.
Column 6, line 10, "referred" should read -- referred to --.
Column 8, line 5 of Claim 1, "having" should read -- having an --.
Column 8, line 3 of Claim 4, "of" should read -- of said --.

Signed and Sealed this

Fourth Day of November, 1997

Attest:

BRUCE LEHMAN

Attesting Officer

Commissioner of Patents and Trademarks